United States Patent [19]

Piche et al.

[11] Patent Number: 5,104,318

[45] Date of Patent: Apr. 14, 1992

[54] IMPLANT ASSEMBLY FOR ANCHORING AN ARTIFICIAL TOOTH

[75] Inventors: Jean Piche, Montreal; Pierre Rochon, Laval sur le Lac, both of Canada

[73] Assignee: 2848-4293 Quebec Inc., Montreal, Canada

[21] Appl. No.: 585,693

[22] Filed: Sep. 20, 1990

[51] Int. Cl.⁵ .............................................. A61C 8/00
[52] U.S. Cl. .................................... 433/174; 433/173
[58] Field of Search ............... 433/172, 173, 174, 175, 433/193, 194

[56] References Cited

U.S. PATENT DOCUMENTS

| | | | |
|---|---|---|---|
| 4,330,891 | 5/1982 | Brånemark et al. | 623/16 |
| 4,713,003 | 12/1987 | Symington et al. | 433/173 |
| 4,824,372 | 4/1989 | Jörnéus et al. | 433/174 |
| 4,850,870 | 7/1989 | Lazzara et al. | 433/173 |
| 4,854,872 | 8/1989 | Detsch | 433/174 |
| 4,988,297 | 1/1991 | Lazzara et al. | 433/173 |

OTHER PUBLICATIONS

Nobelpharma, 1989–1990 product catalog, pp. 3, 13–18.

Primary Examiner—John J. Wilson
Assistant Examiner—Jeffrey A. Smith
Attorney, Agent, or Firm—Foley & Lardner

[57] ABSTRACT

An implant assembly for the anchoring of an artificial tooth in a jawbone comprises a root fixture for anchoring into the jawbone; a metal sleeve resting on top of the root fixture and having a tapering upper section acting as a male element; and a connector element having a lower part secured to the root fixture and an upper part holding the metal sleeve, the upper part being covered by the sleeve. The assembly further includes a combination made up of an artificial tooth having a bore and a counterbore, and a metal insert solid with the tooth and mounted within the counterbore. The insert is cup-shaped at one end and, acts as a female element. It also includes an outwardly flaring internal lateral wall. The tapering upper section and the outwardly flaring lateral wall are shaped and sized so as to fit snuggly one into the other in the manner of a male and female joint (coupling). A screw arrangement tightly secures the tooth combination to the root fixture through the connector element.

12 Claims, 3 Drawing Sheets

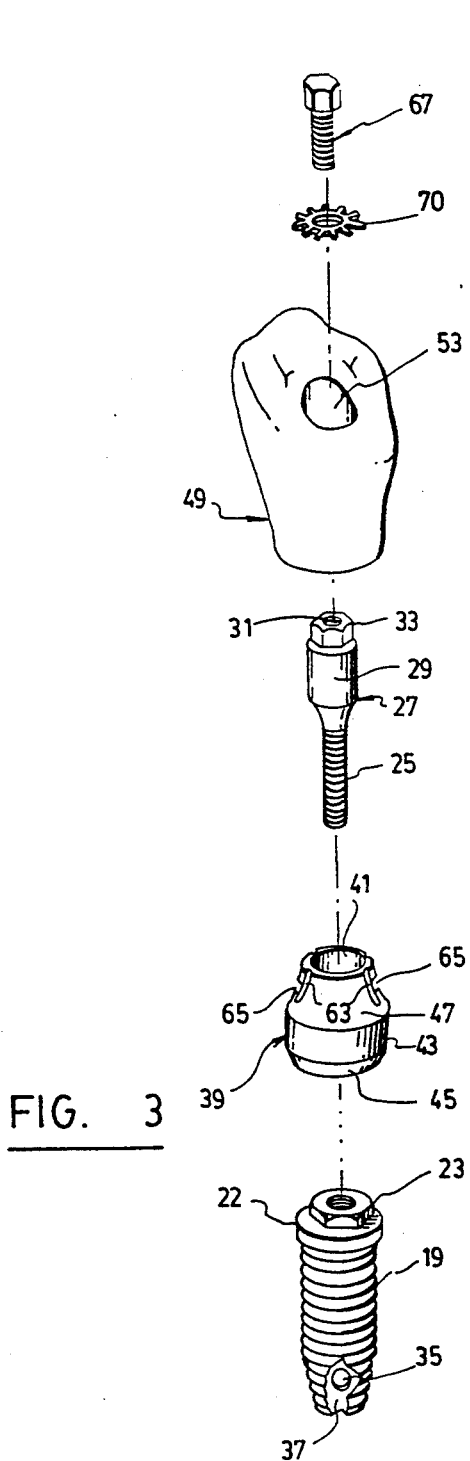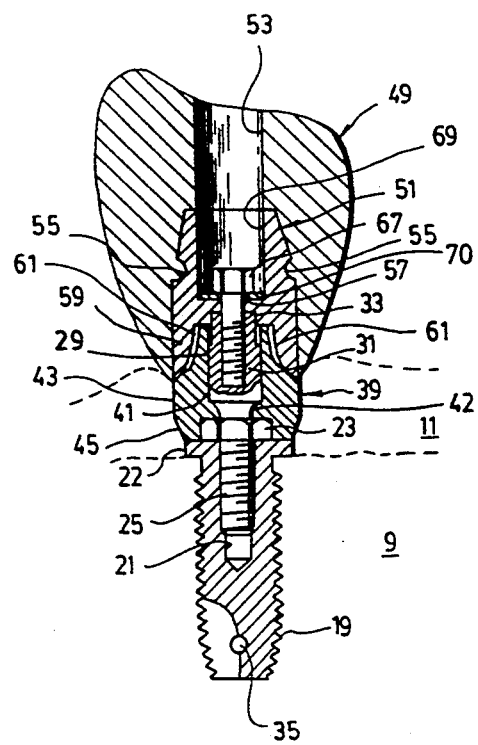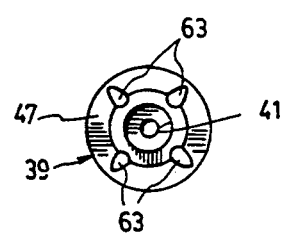
FIG. 3
FIG. 4
FIG. 5

IMPLANT ASSEMBLY FOR ANCHORING AN ARTIFICIAL TOOTH

BACKGROUND OF THE INVENTION

1. Field Of The Invention

The present invention relates to an improved assembly for use in anchoring an artificial tooth in a jawbone.

2. Description Of The Prior Art

An assembly of the above type is known where use is made of a metallic connector sleeve which is mounted, in upright position, above a root fixture secured in the cavity of the jawbone left by the extracted tooth; the sleeve passing through the patient's gum. A tooth combination, which includes an artificial tooth and an insert solid with it, is set squarely over the top of the sleeve and is fastened to the root fixture by means of a screw attachment passing through the insert and the sleeve.

In order to prevent the gum tissue from building up around the connection sleeve and over the heading cap, during the healing period which follows the implantation of the root fixture, the connector sleeve has to be made sufficiently long so as to project safely beyond the top of accumulated gum tissue. However, the upper part of the connector sleeve, which is made of metal such as titanium, then becomes exposed and visible which is of course quite unsightly. The situation may be further aggravated when subsequent resorption of the gum tissue is important.

Another drawback with the known implant assembly is that there is no positive structure to ensure that the tooth combination, and thus the tooth itself, will not eventually rotate on its supporting connector sleeve. While the clamping force applied by the screw attachment mentioned above to fastened the tooth combination on the root fixture may be increased, this can only be done to a limited extent which, in some cases, is found not to be sufficient to prevent eventual tooth rotation.

SUMMARY OF THE INVENTION

A prime object of the invention is therefore to provide an implant assembly as broadly described above wherein the top of the connector sleeve is made so as to fit into the bottom of the tooth insert in the manner of a male and female coupling, the tooth entirely covering the outside of the insert with the connector sleeve being capable of projecting safely beyond the patient's gum. In this way, when the female insert is applied over the male sleeve, after the healing period is completed, any gum tissue that has built around the male sleeve can easily be pushed back against the neck of the tooth which surrounds the insert, thereby completely hiding the metal sleeve from view.

More specifically, the improved implant assembly of the invention comprises a root fixture for anchoring into the jawbone; a metal sleeve having a lower section, the sleeve resting on top of the root fixture and having a tapering upper section acting as a male element; and a connector element adapted to be slid into the sleeve, this element having a lower part adapted to be secured to the root fixture and an upper part covered by the metal sleeve when slid therein and adapted to hold the same onto the fixture. The assembly also comprises a combination made up of an artificial tooth, having a bore and a counterbore, and a metal insert solid with the tooth and mounted within the counterbore. The insert has a cup-shaped end including an outwardly flaring internal lateral wall and acts as a female element. The tapering upper section and the outwardly flaring lateral wall are shaped and sized so as to fit snuggly one into the another in the manner of a male and female coupling. A screw arrangement tightly secures the tooth combination to the root fixture through the connector element.

Another object of the invention is to provide an implant assembly of the above type wherein the male sleeve and the female insert are provided with means, such as joints formed by sets of cooperating tongues and grooves, capable of preventing rotation of the tooth.

Further objects and other features of the invention will become apparent from the description that follows of a preferred embodiment having reference to the appended drawings.

BRIEF DESCRIPTION OF THE DRAWINGS

FIG. 3 is an exploded view, in perspective, of the assembly of FIG. 2;

FIG. 4 is a longitudinal cross sectional view of the assembly of FIG. 2;

FIG. 5 is a top plan view of a connector sleeve, according to the invention.

DESCRIPTION OF THE PREFERRED EMBODIMENT

Figure 1:
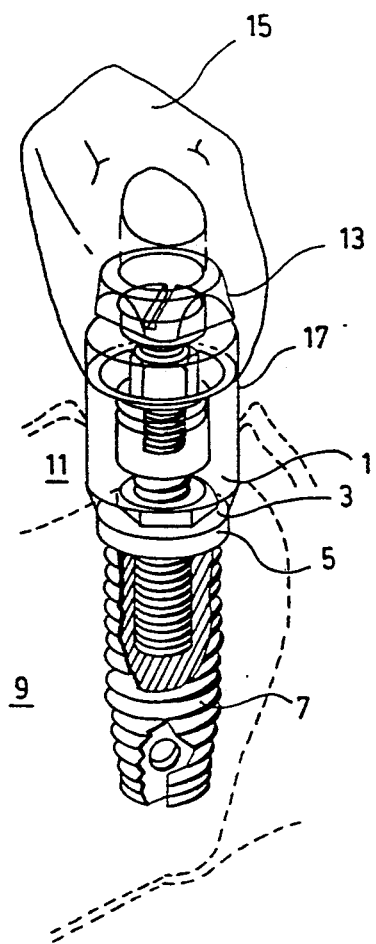
FIG. 1 is a perspective phantom view of a known implant assembly.
Figure 2:
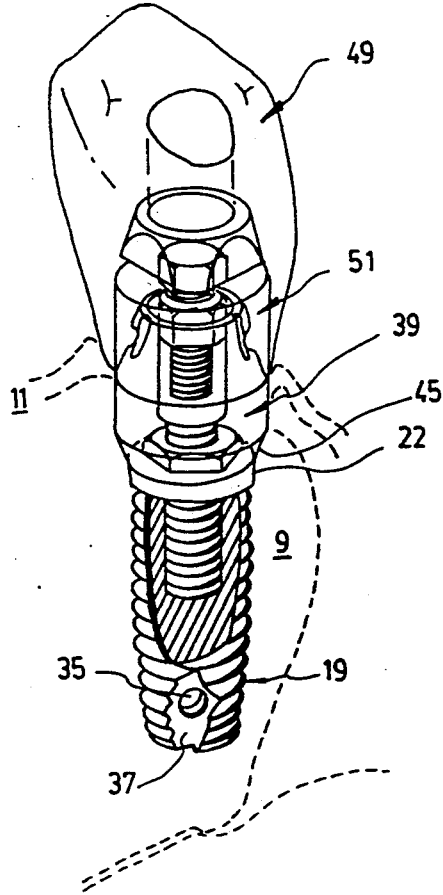
FIG. 2 is a perspective phantom view made according of the invention.
Figure 6:
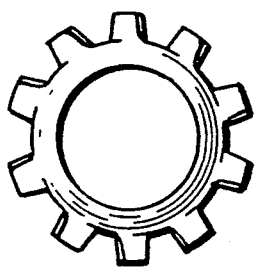
FIG. 6 is a top plan view of a washer for use to lock the screw fixing the tooth to the implant.

Referring to FIG. 1, showing a known tooth implant assembly, a metal connector sleeve 1 is shown mounted in upright position with its lower end 3 seating over the upper flange 5 of a self-tapping root fixture 7 screw threaded into the jawbone 9 covered by gum tissue 11. Squarily set over the end edge of the sleeve 1 is an insert 13 around which is molded an artificial tooth 15 which wholly covers it on the outside, the tooth and insert forming a solid combination. A screw arrangement, of which one example is described hereinafter, ensures tight clamping of the tooth combination 13, 15, and of the connector sleeve 1 on the root fixture 7. As said before and as can be seen from FIG. 1, in order to prevent the gum tissue 11 from building up around the connection sleeve 1 and over a healing cap (not shown), temporarily set over the sleeve 1 during the healing period following the implantation of the root fixture 7, the length (or height) of the sleeve 1 has to be sufficient as to project safely beyond the top of accumulated gum tissue 11 so that the latter will not build over it and over the healing cap. This precaution has, however, a drawback since the top portion 17 of the metal sleeve then remains visible and is consequently unsightly after the healing cap is removed and the tooth combination 13, 15, has been fixed into position. More of the top portion 17 of the sleeve 1 may in fact become visible where resorption of the gum tissue takes place.

Another drawback of the prior art assembly exists, as said above, in that no positive way is provided between the tooth insert 13 and the sleeve 1 to prevent undue rotation of the tooth 15. Indirectly, this could be expected from the screw arrangement tightening the tooth combination and sleeve on the root fixture 7. However, experience shows that is not always the case.

FIGS. 2-6, to which reference is now made, shows one embodiment of the invention where such drawbacks are avoided.

This embodiment makes use of a known root fixture 19, which is a self-tapping titanium screw driven into the cavity left in the bone 9 by the extraction of the tooth. It has a blind bore 21 at the top of which, and over a shoulder 22, is coaxally fixed, in any convenient way, a polygonal nut 23 that can be outwardly extending as shown in the drawings or be inwardly positioned in a counterbore (not shown). Threaded through said nut and entering the bore 21 is the threaded lower part 25 of a titanium connector element 27 of which the upper part 29 is formed with a blind bore 31 having a coaxial nut 33 mounted fast at its open end. As will be understood, rotation of the nut 33 causes fastening of the connector element 27 to the root fixture 19. The latter is drilled, at its lower end, with a hole 35 which becomes invested with the tissue of the jawbone 11 so as further to prevent undue rotation of the fixture 19. Additionnally, a cavity 37 (FIG. 3) may be left for the same purpose.

Prior to being accured by threading to the root fixture 19, the connector element 27 is inserted into a titanium sleeve 39 formed, for that purpose, with a bore 41 that is provided with an inwards retaining flange 42 at its lower end and is followed by a polygonal counterbore into which the nut 23 fits to prevent rotation of the sleeve 39 relative to the root fixture 19, when this nut extends outwardly. When the nut 23 is located in a counterbore provided in the upper end of the fixture 19, the lower end of the sleeve 39 may be provided with a polygonal annular projection sized to fit into this counterbore.

After such a insertion, the upper part 29 of the connector element is located inside the bore 41 and thus covered by the sleeve 39. This upper part 29 is wider than the threaded lower part 25 and bears against the flange 42, thus holding the sleeve 39 onto the fixture 19. It will be noted from FIG. 4 that, once in position over the root fixture 19, nut 33 projects slightly above the top of the sleeve 39.

The sleeve 39 has a lower section 43 which is essentially cylindrical and may be 1 to 5 mm high. It preferably has a chamfered lower end 45 to fit any size of root fixture 19, which preferably joins a shoulder 22 of the fixture 19. Its upper section 47 tapers however from the lower section 43 and is preferably concave.

Set over the sleeve 39 is a tooth combination made up of an artificial ceramic tooth 49 and of a titanium insert 51. The tooth is molded around the insert while a bore 53 is created; the insert 51 itself acting as a core making a counterbore into which it is wholly received, as shown, with the neck of the tooth terminating at the lower tip of the insert so that the latter is not visible from the outside. A set of circumferentially spaced outer grooves 55 is provided around the insert to insure that it becomes solid with the tooth and that the tooth will not tend to rotate relative to it. The insert 51 is shaped as an inverted cup, at one end, including a straight transverse bottom wall or bridge 57, having a screw hole at its center, and a lateral wall 59 flaring outwardly from the bottom wall 57. Complementary to the upper section 47 of the connector sleeve 39, the outwardly flaring lateral wall 59 is preferably convex. As can be gathered from FIGS. 3 and 4, both the upper section 47 of the sleeve 39 and the lateral wall 59 of the insert 51 are circular in cross section and are sized and shaped such that the lateral wall 59 fits snuggly over the upper section 49 with the bottom wall 57 standing slightly above the nut 33 of the connector element 27.

Adequate means are provided in order to prevent relative rotation between the tooth combination 49, 51, and the sleeve 39. Such means may be joints in the form of axially extending ribs or tongues 61, projecting from the inner face of the outwardly facing lateral wall 59 of the insert 51 (FIG. 4); these ribs 61 fitting into complementary grooves 63 (FIGS. 3,5) of the connector sleeve 39. Notches 65 may also be provided on the concave upper section 47 for the insertion of jaws of handling grippers.

The tooth combination is securely fixed to the root fixture 19 by a gold screw 67 inserted successively through the bore 53 of the tooth 49, a coaxial bore 69 of the insert 51, the previously mentioned hole through the insert bottom or bridge 57 and threaded into the nut 33 solid with the connector element 27 which is itself tightly screwed into the nut 23 solid with the root fixture 19. A washer 70 provided with a plurality of radially extending twisted pins as better shown in FIG. 6 may be used to lock the screw 67 when it is being threaded.

When the assembly is completed, the bridge 57 comes in abutment against the top of the sleeve 39 or, preferably, the outer tip of the insert of the insert flaring wall 59 comes to butt against the inner end of the tapering upper section 47 of the sleeve 39.

While the securing screw 67 has been said to be made of gold and the root fixture 19, the connector sleeve 39 and the insert 51 made of titanium, it will be understood of course that they may be made of any other suitable material.

The embodiments of the invention in which an exclusive property of privilege is claimed are defined as follows:

1. An implant assembly for the anchoring of an artificial tooth in a jawbone, said assembly comprising:
   a root fixture constructed to be anchored into the jawbone;
   a metal sleeve having a lower section resting on top of said root fixture and a tapering upper section acting as a male element, said upper section being formed with a bore opening at the top thereof, said bore defining a retaining flange within said sleeve;
   a connector element adapted to be slid into the sleeve, said element having a lower part adapted to be secured to said root fixture and an upper part projecting above said lower part, said upper part being wider than said lower part and sized to be slidably received into said bore in the upper section of the sleeve, wherein when said connector element is slid into said sleeve, said upper part is covered by said sleeve and bears on said retaining flange to hold said sleeve onto said fixture;
   a tooth combination including an artificial tooth having a bore and a counterbore therethrough, said combination further including a metal insert solid with said tooth and mounted within said counterbore; said insert having a cup-shaped end including an outwardly flaring internal lateral wall; said insert having a cup-shaped end including an outwardly flaring internal lateral wall; said insert being further shaped and sized for said outwardly flaring lateral wall to fit snugly over said sleeve tapering upper section;

means on said sleeve tapering section and on said outwardly flaring lateral wall of said insert for preventing relative rotation between said tooth combination and said sleeve; and means for tightly securing said tooth combination to said root fixture through said connector element.

2. An assembly as claimed in claim 1, wherein said sleeve tapering upper section is concave and said insert outwardly flaring lateral wall is convex.

3. An assembly as claimed in claim 1, wherein said rotation-preventing means are axial tongues and grooves adapted to form joints and provided respectively on said insert flaring lateral wall and on said sleeve tapering section.

4. An assembly as claimed in claim 1, wherein said insert flaring lateral wall and said sleeve upper and lower sections are circular in transverse cross section.

5. An implant assembly for the anchoring of an artificial tooth in a jawbone, said assembly comprising:

a root fixture constructed to be anchored into the jawbone;

a metal sleeve having a lower section resting on top of said root fixture and a tapering upper section acting as a male element;

a connector element adapted to be slid into the sleeve, said element having a lower part adapted to be secured to said root fixture and an upper part projecting above said lower part, said upper part being covered by said sleeve when slid therein and adapted to hold said sleeve onto said fixture;

a tooth combination including an artificial tooth having a bore and a counterbore therethrough, said combination further including a metal insert solid with said tooth and mounted within said counterbore; said insert having a cup-shaped end including an outwardly flaring internal lateral wall; said insert being further shaped and sized for said outwardly flaring lateral wall to fit snugly over said sleeve tapering upper section;

means for tightly securing said tooth combination to said root fixture through said connector element; and wherein said sleeve tapering upper section is concave and said insert outwardly flaring lateral wall is convex.

6. An implant assembly for the anchoring of an artificial tooth in a jawbone, said assembly comprising:

a root fixture constructed to be anchored into the jawbone;

a metal sleeve having a cylindrical lower section resting on top of said root fixture and an upper section tapering from said lower section said upper section being formed with a bore opening at the top thereof, said bore defining a retaining flange within said sleeve;

a connector element adapted to be slid into the sleeve, said element having a lower part secured to said root fixture and an upper part projecting above said fixture, said upper part being wider than said lower part and sized to fit into said bore in the upper section of the sleeve, wherein when said connector element is slid into said sleeve, said upper part is covered by said sleeve and bears on said retaining flange to hold said sleeve onto said fixture; said upper part being formed with a bore opening at the top thereof;

a nut solid with said upper part at the top thereof and coaxial with said bore of said upper part;

a tooth combination including an artificial tooth having a bore and a counterbore therethrough, said combination further including a metal insert solid with said tooth and mounted wholly within said tooth counterbore; said insert having a cup-shaped end including a transverse bottom wall, formed with a screw hole therethrough, and a lateral wall flaring outwardly from said bottom wall; said insert being further shaped and sized for said outwardly flaring lateral wall to fit snugly over said sleeve tapering upper section with said bottom wall standing above said nut of said connector element;

means on said sleeve tapering section and on said outwardly flaring lateral wall of said insert for preventing relative rotation between said tooth combination and said sleeve; and a securing screw having a stem passing through said screw hole of said bottom wall, threading into said nut of said connector element and extending into the bore at the top thereof, the head of said screw resting on said insert bottom wall, wherein said screw clamps said tooth combination on said connector element.

7. An assembly as claimed in claim 6, wherein said sleeve tapering upper section is concave and said insert outwardly flaring lateral wall is convex.

8. An assembly as claimed as in claim 6, wherein said rotation-preventing means are axial tongues and grooves forming joints and provided respectively on said insert flaring lateral wall and on said sleeve tapering section.

9. An assembly as claimed in claim 6, wherein said insert flaring lateral wall and said sleeve upper and lower sections are circular in transverse cross section.

10. An assembly as claimed in claim 6, wherein
said sleeve has a counterbore having a polygonal shape opposite said bore in said sleeve;
said root fixture is formed with an open bore and a nut is fixed to said fixture at the open end of said fixture bore;
said lower part of said connector element is a screw threaded through said fixture nut and extending into said fixture bore; and
said sleeve polygonal bore fits over said nut to prevent relative rotation between said sleeve and said root fixture.

11. An assembly as claimed in claim 10, wherein said rotation preventing means are axial tongues and grooves forming joints and provided respectively on said insert flaring lateral wall and on said sleeve tapering section.

12. An assembly as claimed in claim 10, wherein said insert flaring lateral wall and said sleeve upper and lower sections are circular transverse cross section.

* * * * *